US005601086A

United States Patent [19]
Pretlow, III et al.

[11] Patent Number: 5,601,086
[45] Date of Patent: Feb. 11, 1997

[54] BEAT FREQUENCY ULTRASONIC MICROSPHERE CONTRAST AGENT DETECTION SYSTEM

[75] Inventors: Robert A. Pretlow, III, Kirkland, Wash.; William T. Yost, Newport News; John H. Cantrell, Jr., Yorktown, both of Va.

[73] Assignee: The United States of America as represented by the Administrator of the National Aeronautics and Space Administration, Washington, D.C.

[21] Appl. No.: 440,266

[22] Filed: May 12, 1995

[51] Int. Cl.⁶ .................................... A61B 8/06
[52] U.S. Cl. .................................... 128/662.02
[58] Field of Search .......... 128/660.02, 662.01, 128/662.02; 73/861.25

[56] References Cited

U.S. PATENT DOCUMENTS

| | | | |
|---|---|---|---|
| 4,316,391 | 2/1982 | Tickner | 73/861.25 |
| 4,391,149 | 7/1983 | Herzl | 73/861.25 |
| 4,483,345 | 11/1984 | Miwa | 73/19 |
| 4,608,993 | 9/1986 | Albert | 73/861.25 X |
| 5,135,000 | 8/1992 | Akselrod et al. | 128/662.02 |
| 5,195,520 | 3/1993 | Schlief et al. | 128/660.02 |
| 5,255,683 | 10/1993 | Monaghan | 128/662.02 |
| 5,348,015 | 9/1994 | Moehring et al. | 128/661.07 |
| 5,402,393 | 3/1995 | Konrad | 367/89 |
| 5,410,516 | 4/1995 | Uhlendorf et al. | 367/7 |
| 5,456,257 | 10/1995 | Johnson et al. | 128/662.02 |
| 5,485,841 | 1/1996 | Watkin et al. | 128/660.01 |

OTHER PUBLICATIONS

Schrope et al, "Simulated capillary blood flow measurement using a nonlinear ultrasonic contrast agent", *Ultrasonic Imaging*, 14, (1992) pp. 134–158.

*Primary Examiner*—Francis Jaworski
*Attorney, Agent, or Firm*—Robin W. Edwards

[57] ABSTRACT

A system for and method of detecting and measuring concentrations of an ultrasonically-reflective microsphere contrast agent involving detecting non-linear sum and difference beat frequencies produced by the microspheres when two impinging signals with non-identical frequencies are combined by mixing. These beat frequencies can be used for a variety of applications such as detecting the presence of and measuring the flow rates of biological fluids and industrial liquids, including determining the concentration level of microspheres in the myocardium.

11 Claims, 6 Drawing Sheets

BEAT FREQUENCY ULTRASONIC MICROSPHERE CONTRAST AGENT DETECTION SYSTEM

ORIGIN OF THE INVENTION

The invention described herein was jointly made by employees of the United States Government and in the performance of work under a NASA Contract and is subject to the provisions of Section 305 of the National Aeronautics and Space Act of 1958, as amended, Public Law 85-568 (72 Stat. 435; 42 USC 2457).

BACKGROUND OF THE INVENTION

1. Eield of the Invention

This invention relates generally to ultrasonically-reflective microsphere contrast agents for ultrasonic imaging and more particularly to the quantitative detection of microspheres in biological applications.

2. Description of the Related Art

Ultrasonically-reflective microsphere contrast agents are used in medical ultrasonic imaging to enhance the image obtained by increasing the contrast of and outlining the anatomic structures being studied, for example the heart (its chambers, blood vessels, and tissue). An example of such an agent is Albunex, available from Molecular Biosystems, San Diego, Calif. Microsphere contrast agents are also used to ultrasonically assess adequacy of blood flow (i.e., perfusion) to the heart muscle (i.e., myocardium). Assessment of perfusion allows determination of the existence or risk of a myacardial infarction (i.e., a heart attack), in which the heart muscle dies because of blockage by plaque of the blood vessels supplying it.

Currently, microsphere contrast agents must be injected directly into the arteries of the heart muscle in order to be detectable with conventional ultrasonic scanners (via video intensity) and to thereby allow assessment of myacardial perfusion. Consequently, this technique is available only during cardiac surgery or catheterization. Non-invasive procedures such as peripheral intraveneous injection of the microspheres are desirable. However, dilutional effects and trapping of the larger, more reflective microspheres by the lung circulation lowers the effective microsphere concentration to such a degree that conventional ultrasonic scanners can no longer detect them in the myacardium.

Monaghan (U.S. Pat. No. 5,255,683) discloses a method of microsphere detection based on a shift in the radiofrequency (RF) spectrum of the ultrasonic myocardial echo when microspheres are present. This method is used to assess myocardial perfusion in patients. This spectral shift method does not involve the mixing of two frequencies by the microspheres with a subsequent emission of a third frequency by the microspheres. The method disclosed by Monaghan is only a qualitative detector of microsphere presence or absence. It does not allow quantitative estimation of the microsphere level in the myocardium and thus has limited use in assessing myocardial perfusion.

Shrope et al. in *Ultrasonic Imaging* 14(2), April 1992, investigated a method of detection based on generation by the microspheres of an RF second harmonic of the transmitted scanner frequency. As the second harmonic generated by the myocardium is of much lower magnitude, presence of the harmonic correlates with presence of the microspheres. Microsphere level in the myocardium per unit time can thus be measured and myocardial perfusion derived. The second harmonic detection method, however, requires that the microspheres have a fairly specific shell type, and will currently work only with specific agents such as SHU508 (available from the Schering Corp. in Germany).

Albert (U.S. Pat. No. 4,608,993) discloses measuring blood flow using the Doppler shift of ultrasound by blood components in a blood vessel. However, this non-invasive technique does not use microsphere contrast agents.

SUMMARY OF THE INVENTION

In accordance with one aspect of the present invention, a method and system for ultrasonically examining tissue using an ultrasonically-reflective microsphere contrast agent detects the presence of ultrasonic beat frequencies generated by the presence of the microspheres.

More specifically, in accordance with this aspect of the present invention, a method of examining tissue using ultrasonically-reflective microsphere contrast agents detects non-linear sum and difference beat frequency signals which are produced when two signals with non-identical frequencies are combined by mixing. The amplitude of these beat frequencies is used to determine the concentration level of the microspheres in the myocardium. In the myocardium, the microspheres act as non-linear ultrasonic mixers when impinged upon by two or more ultrasonic waves of different frequencies. The microspheres re-radiate both the impinging frequencies, but in addition they generate non-linear difference and sum frequencies. This non-linear effect is significantly greater when one or both impinging frequencies approximates the resonant frequency of the microspheres. Myocardial tissue, on the other hand, reflects the two original frequencies since the myocardium does not generate substantial amplitudes of sum or difference frequencies.

To produce the beat frequencies, an insonifier transducer instills ultrasonic energy into a patient's chest at a prescise single frequency, ideally the resonant frequency of the microspheres. A scanner transducer also instills ultrasonic energy into the patient's chest at a single frequency, but the scanner frequency is different than that of the insonifier. In addition, the scanner receives and processes the ultrasonic echo and generates a video image. The beat frequency signal due to the microspheres in the myocardial region of interest is detected within the overall echo signal. A plot is then generated of the microsphere signal level vs. time, which in turn correlates with myocardial perfusion. Myocardial perfusion parameters are derived such as: time to peak of curve, time to half peak (ascending and descending portions of curve), half-time point slopes, time of appearance of contrast agent, and area under the curve.

The present invention permits the detection of the relatively small level of microspheres passing through the myocardium per unit of time after peripheral intraveneous injection. In addition, the present invention derives myocardial perfusion parameters from this data. Advantages of the present invention include both the ability to quantitatively detect small levels of microspheres in heart tissue and the ability to use this method with all types of microsphere and microbubble contrast agents.

DESCRIPTION OF THE PREFERRED EMBODIMENTS

Figure 1:
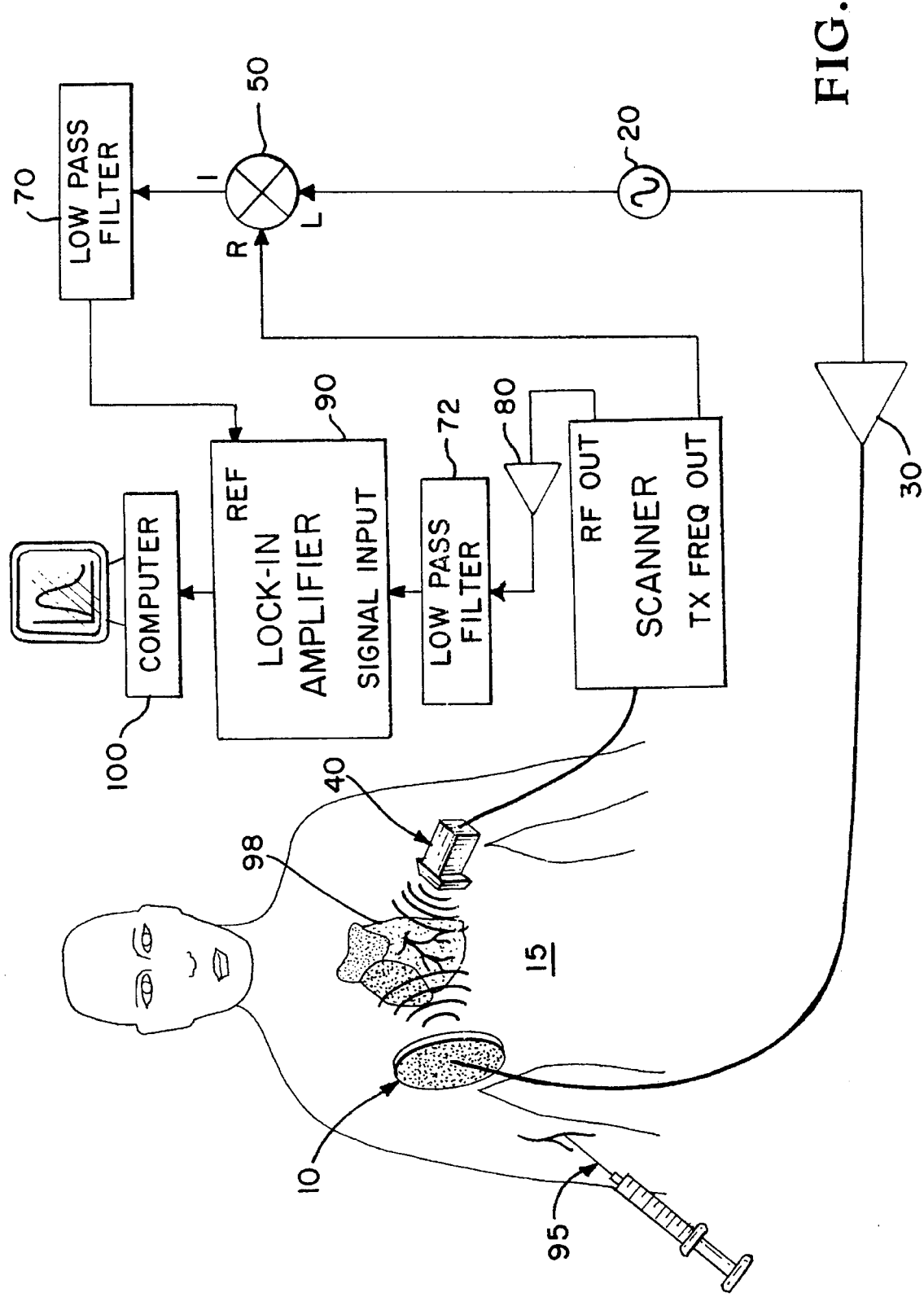
FIG. 1 is a block diagram of one embodiment of the present invention in which myocardial perfusion is measured.

Referring to FIG. 1, the insonifier transducer 10 instills ultrasonic energy into a patient's chest 15 at the resonant frequency of the microsphere contrast agent, e.g., 1.3 MHz for Albunex. The term microsphere as used in this specification should be understood to include the use of microbubbles. The insonifying signal originates from a signal generator 20, is amplified by the RF power amplifier 30, and is then fed to the insonifying transducer 10. The scanner transducer 40 also instills ultrasonic energy into the patient's chest 15 at a single frequency, but the scanner frequency is different than that of the insonifier. The intersection of the two beams of ultrasonic energy form an intersection volume which, in this example corresponds to a portion of the myocardium 98. Typical scanner frequencies that are used in medical applications are 1.0 MHz to 5.0 MHz, but other frequencies may also be used. The limit on the frequency used is the attenuation of the amplitude of the insonifying signal and the requirement that the frequency approximately match a resonant frequency of the microspheres. For example, for structures close to the surface, such that attenuation of the ultrasonic wave is not an important factor for the insonifying frequency, frequencies ranging up to 30 Mhz could easily be used. The scanner 40 also receives and processes the ultrasonic echo and generates a video image. The received image is used to locate a region of interest to evaluate myocardial perfusion by means of the microsphere detection method of the present invention.

Although the present invention is illustrated in reference to circulation dynamics of arterial blood flow in myocardial tissue, this apparatus and method has broader application to any body organ, body tissue or body fluid where alteration in fluid or tissue dynamics is central to the pathology under investigation. For example, with the use of suitable microspheres, the present invention can be used to monitor blood flow patterns in the brain of stroke patients, tumors, retinal blood flow in the eye, tissues affected by pressure ulcers, and blood perfusion of any tissue in any part of the human body, including muscle and tendon tissue. Additionally, the invention can be used to enhance images of fluids and tissue in any part of the body. The beat frequency signal image can be superimposed on conventional scanning images to reveal anatomy not otherwise visible to clinicians.

The interface electronics consist of a mixer 50, two lowpass filters 70 and 72, a signal amplifier 80, and a lock-in amplifier 90. When microspheres 95 are injected into the patient and reach the myocardium 98, the signal due to the microspheres 95 in the myocardial region of interest is detected within the overall echo signal. A plot is then generated of the microsphere signal level vs. time, which in turn correlates with myocardial perfusion.

Figure 2:
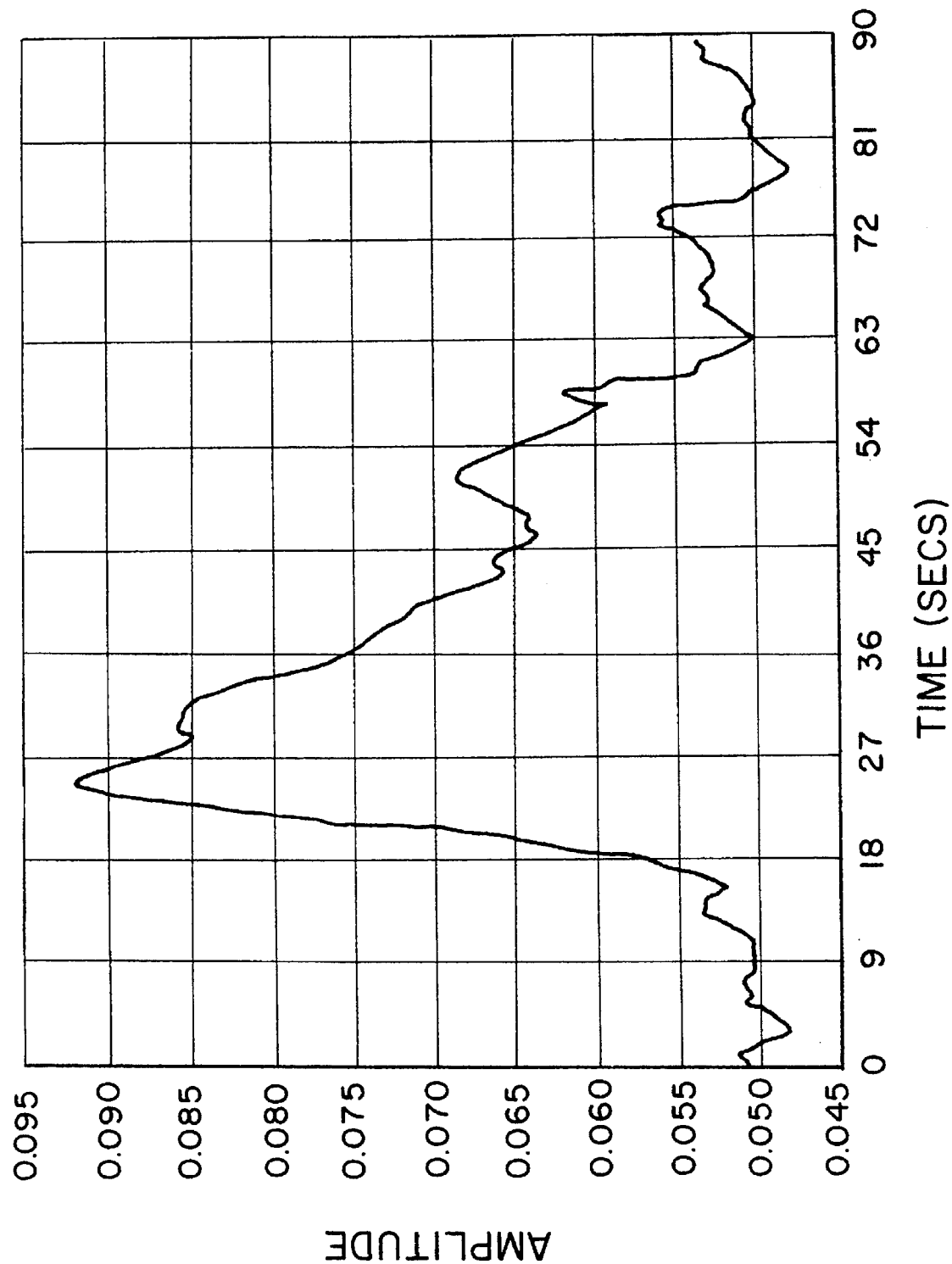
FIG. 2 is a typical plot of difference frequency signal amplitude versus time for Albunex microspheres passing through a body tissue circulation area such as the myocardium.

A computer 100 controls the operation of the system, plots microsphere concentration vs. time, and derives myocardial perfusion parameters. Such perfusion parameters would include: time to peak of curve, time to half peak (ascending and descending portions of curve), half-time point slopes, time of appearance of contrast agent, and area under the curve. FIG. 2 illustrates a typical frequency amplitude versus time curve from which perfusion parameters can be derived.

The present invention uses ultrasonic beat frequencies generated by the injected microspheres 95 to detect their presence and concentration level in the myocardium 98. Beat frequencies are produced when two signals with non-identical frequencies are combined by mixing. Non-linear sum and difference frequencies result, according to the following trignometric identity:

$$\mathrm{Cos}(A)\mathrm{Cos}(B) = \tfrac{1}{2}\mathrm{Cos}(A+B) + \tfrac{1}{2}\mathrm{Cos}(A-B)$$

Figure 3:
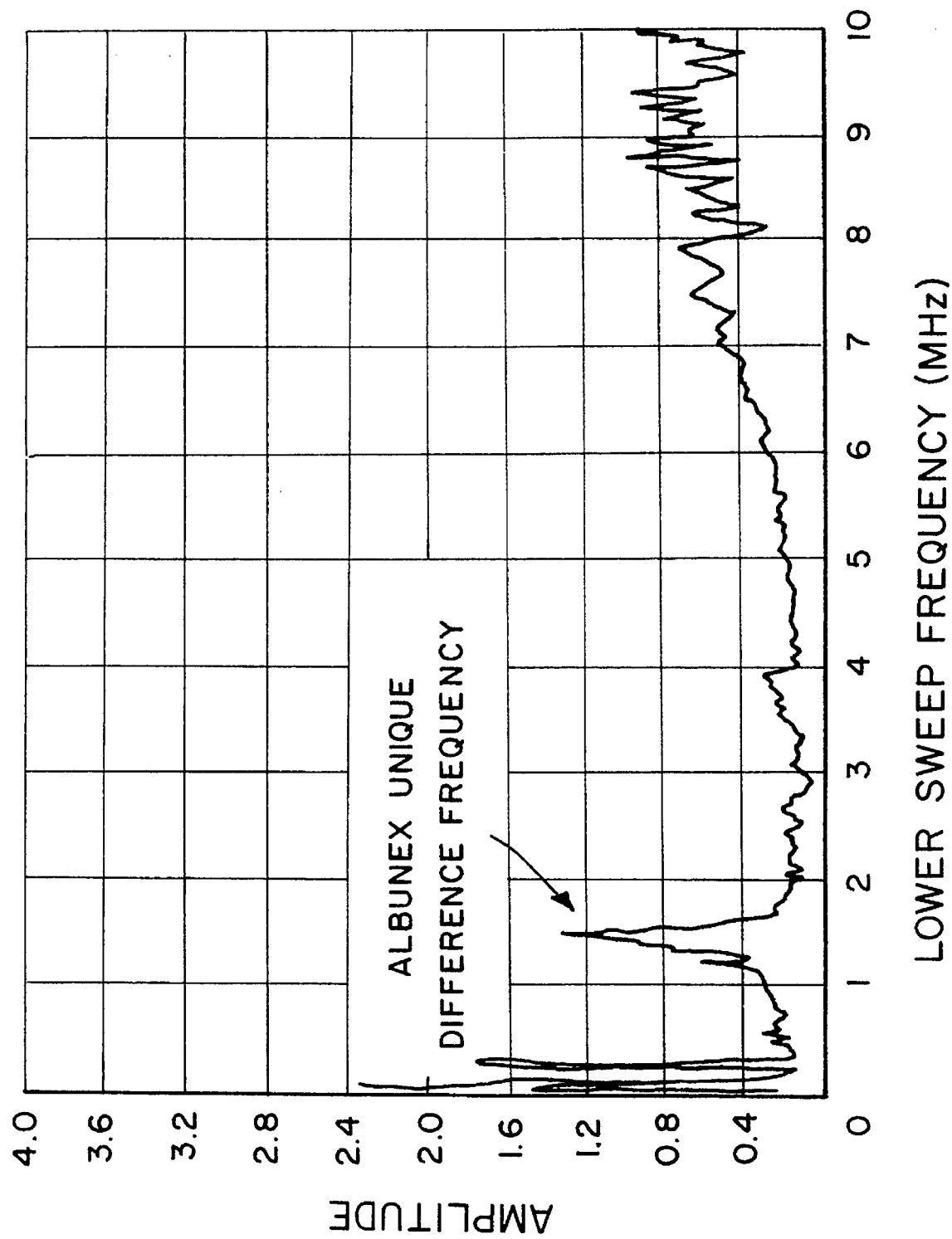
FIG. 3 is a plot of difference frequency signal amplitude versus insonifying frequency for Albunex microspheres.
Figure 4:
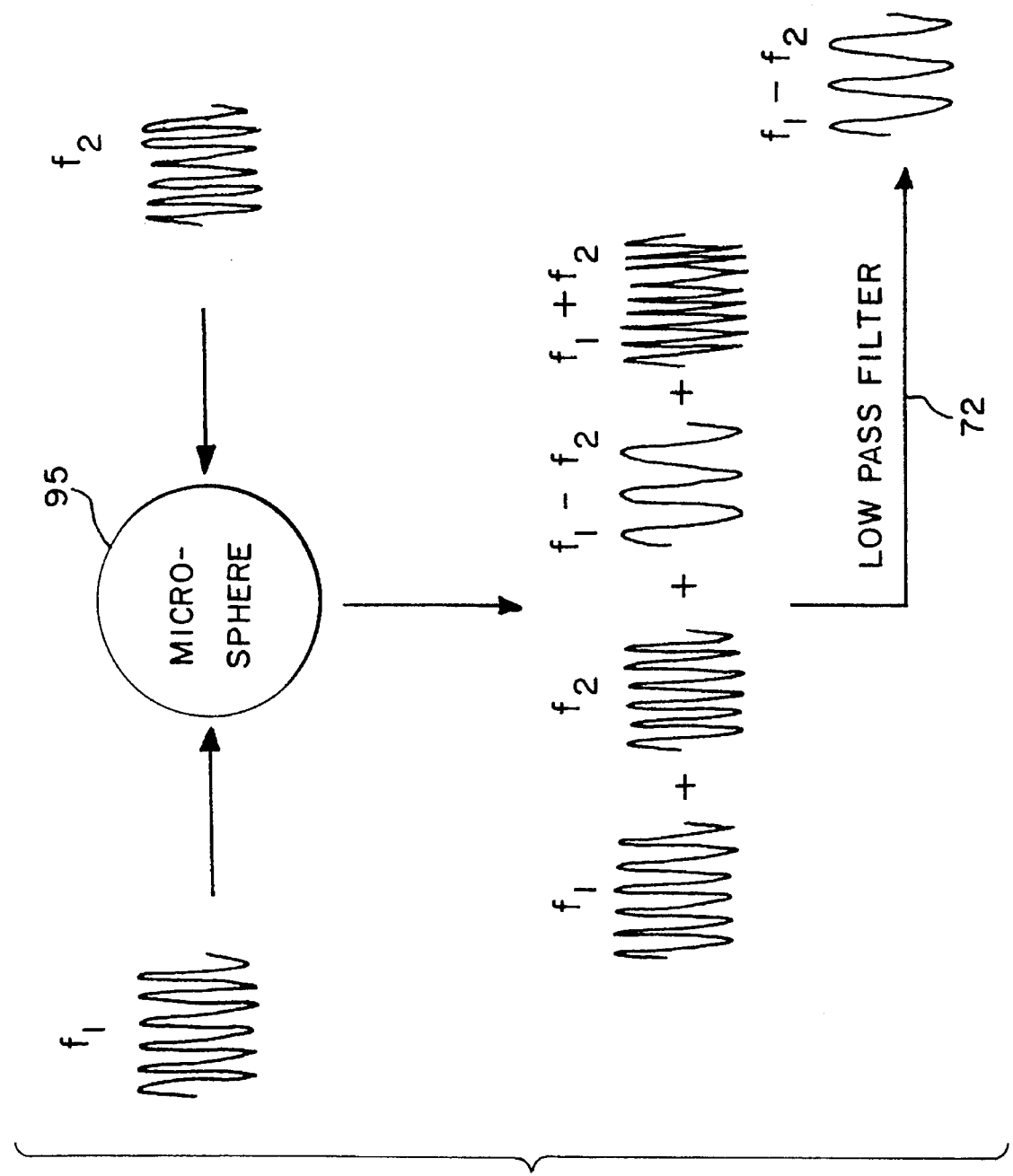
FIG. 4 is a graphical example of the generation of sum and difference signals by the microspheres.

Referring to FIGS. 3 and 4, in the myocardium 98, the microspheres 95 act as non-linear ultrasonic mixers when impinged upon by two or more ultrasonic waves of different frequencies. The microspheres re-radiate both the insonifying and the scanner frequencies, but in addition they generate non-linear difference and sum frequencies. This effect increases dramatically when the insonifying frequency is near the microsphere resonant frequency. FIG. 3 shows that for Albunex, the effect peaks markedly at about 1.3 Mhz which is the Albunex resonant frequency. Referring to FIG. 4, if the scanner probe 40 instills $f_2$ at 2 MHz and the insonifying transducer 10 instills $f_2$ at 1.3 MHz, the sum ($f_1+f_2$) and difference ($f_1-f_2$) frequencies generated by the microspheres would be 3.3 MHz and 0.7 MHz, respectively. Myocardial tissue, on the other hand, reflects the scanner and insonifying frequencies but does not generate significant sum or difference frequencies. Myocardial generation of significant sum and difference frequencies would occur only if the insonifying frequency were near the myocardium resonant frequency.

To determine the concentration of the microspheres, consider two intersecting beams, one with a frequency $f_1$ and the other with frequency $f_2$, as illustrated in FIG. 4. The purpose of the measurement is to determine at any instant the concentration of microspheres in the insonified region, which is defined geometrically by the volume intersection or interaction volume of the two beams. Each microsphere in the interaction volume will respond by generating the mixing components of the two frequencies, $f_1$ and $f_2$ ($f_1+f_2$, $f_1-f_2$, $2f_1$, $2f_2$, and to a lesser extent, $3f_1$, $3f_2$, and other non-linear products). The magnitude of the received signal of each mixing component depends upon $A_1$, the amplitude of $f_1$, $A_2$, the amplitude of $f_2$, the total number of microspheres in the insonified region, and the microsphere mixing efficiency, which depends upon microsphere properties (e.g., resonance) and acoustic wavelengths, amplitudes, frequencies and phase relationships.

With known drive amplitudes $A_1$ and $A_2$, one can use a direct measurement with a calibrated (receive) transducer and knowledge of the tissue attenuations in the respective insonifying beam paths to determine the concentration of microspheres in the interaction volume. One way is to develop a tissue phantom which is placed between the drive transducers and the difference frequency sensing device.

When the drive transducers are activated with specific drive waveforms, the calibration is made from measurements of the mixed frequencies from a known concentration of microspheres in the interaction volume. With a determination of the size of the insonified volume in the patient, the only unknown is the actual microsphere concentration, which therefore can be calculated from measurement and comparison with the calibration results. The larger the amplitude of the in, sonifying waves, the greater is the amplitude of the detected wave and therefore the quicker the scan that can be performed.

The frequency $f_1-f_2$ would be the lowest frequency component, and hence it would most likely be the most easily received of the mixing components, since it would be the least affected by tissue attenuation. Therefore, it will be used to illustrate the present invention, although any mixing component could be used. Once the difference frequency is generated, it must traverse the tissue between the generating microsphere and the transducer or transducer array. The output from this transducer is analyzed to determine microsphere concentration. This analysis can be done by computer algorithm or other analytical means. The microspheres in the interaction volume of the two ultrasonic waves, each wave at its respective drive frequency, will be appropriately activated.

The frequencies $f_1$ and $f_2$ are chosen (1) so that either $f_1$ or $f_2$ approximates the resonant frequency of the microspheres but differs from the resonant frequency of the tissue to be examined and (2) so that the output of the difference frequency receiver transducer is maximized. Other considerations which affect the decision are tissue attenuation to $f_1$ and $f_2$, distance of activation volume from the $f_1$ and $f_2$ drive transducers, location of the difference frequency transducer, and the efficiency of microsphere generation of the difference frequency $f_1-f_2$.

For example, if one is examining a region near the junction of muscle fibers to the tendon which attaches the muscle to the bone, the drive transducers could be spaced 60° apart on the arc of a circle where the area under examination is located at the center. The receiver transducer, sensitive to the difference frequency $f_1-f_2$, can be placed on the same circle but located 150° from either insonifying transducer. Under these conditions, the ultrasonic waves generated by the insonifying transducers intersect at the area in question and the wave of frequency $f_1-f_2$ generated by the microspheres will propagate from the insonified volume at the center of the circle to the receive transducer. The output of the receive transducer is then proportional to the concentration of microspheres within the insonified volume.

After the selection of the drive frequencies, the receive transducer is chosen to optimize the sensitivity to the drive frequency. The order of importance in selecting the drive frequencies will be largely determined by the particular application. For example, if the region to be examined is approximately 5 cm deep and the receive transducer is placed directly below the area of examination, the following factors will be important in selecting the drive frequencies: (1) the efficiency of mixing of the two insonifying ultrasonic waves by the microspheres, (2) the attenuation of neighboring tissue through which the insonifying ultrasonic waves must pass to reach the interaction volume, (3) the depth of the interaction volume from the drive transducers, and (4) an acceptable site location for the receive transducer.

A high-gain, extremely narrow-band amplifier circuit 90 (lock-in amplifier) detects precisely the difference frequency generated by the microspheres 95. It does this by comparing the incoming RF signal to an exact difference reference signal derived from electronically mixing the scanner transmit frequency and the chest insonifying frequency and lowpass filtering the result. The incoming RF echo signal contains both the myocardial tissue signal and the microsphere-generated signal consisting of the scanner, insonifying, sum and difference signals. The incoming RF echo signal also contains noise. A lowpass filter 72 is used to allow passage of only the difference frequency and the low frequency component of the noise to the lock-in amplifier circuit input. The lock-in amplifier circuit function can be understood by the following:

Let:

$A\cos(X)$=electronically-generated difference signal (reference signal)

$[B\cos(Y)+n(t)]$=microsphere-generated difference signal (desired signal) plus noise, which constitutes the lowpass filtered incoming RF signal.

The lock-in circuit 90 first electronically mixes the lowpass filtered incoming RF signal with the reference signal:

$$A\cos(X)[B\cos(Y)+n(t)]=\tfrac{1}{2}AB\cos(X+Y)+\tfrac{1}{2}AB\cos(X-Y)+n(t)A\cos(X)$$

If X=Y, then:

$$=\tfrac{1}{2}AB\cos(2X)+\tfrac{1}{2}AB+n(t)A\cos(X)$$

Lowpass filtering the result gives:

$=\tfrac{1}{2}AB$ i.e., a DC value which is proportional to the amplitudes of the reference signal and the desired microsphere signal.

If the reference amplitude is held constant, then the result is a DC value proportional to only the microsphere-generated difference signal. The lock-in amplifier circuit 90 can detect the microsphere signal even when the incoming RF signal is highly contaminated with noise of much greater amplitude. The lock-in function can be accomplished by either analog or digital (i.e., software) means. The output of the lock-in amplifier 90 consists of the amplitude of the microsphere difference frequency detected. Detection of the signal due to the microspheres is thus possible even at very low concentrations such as in the myocardium after peripheral intravenous injection.

Figure 5:
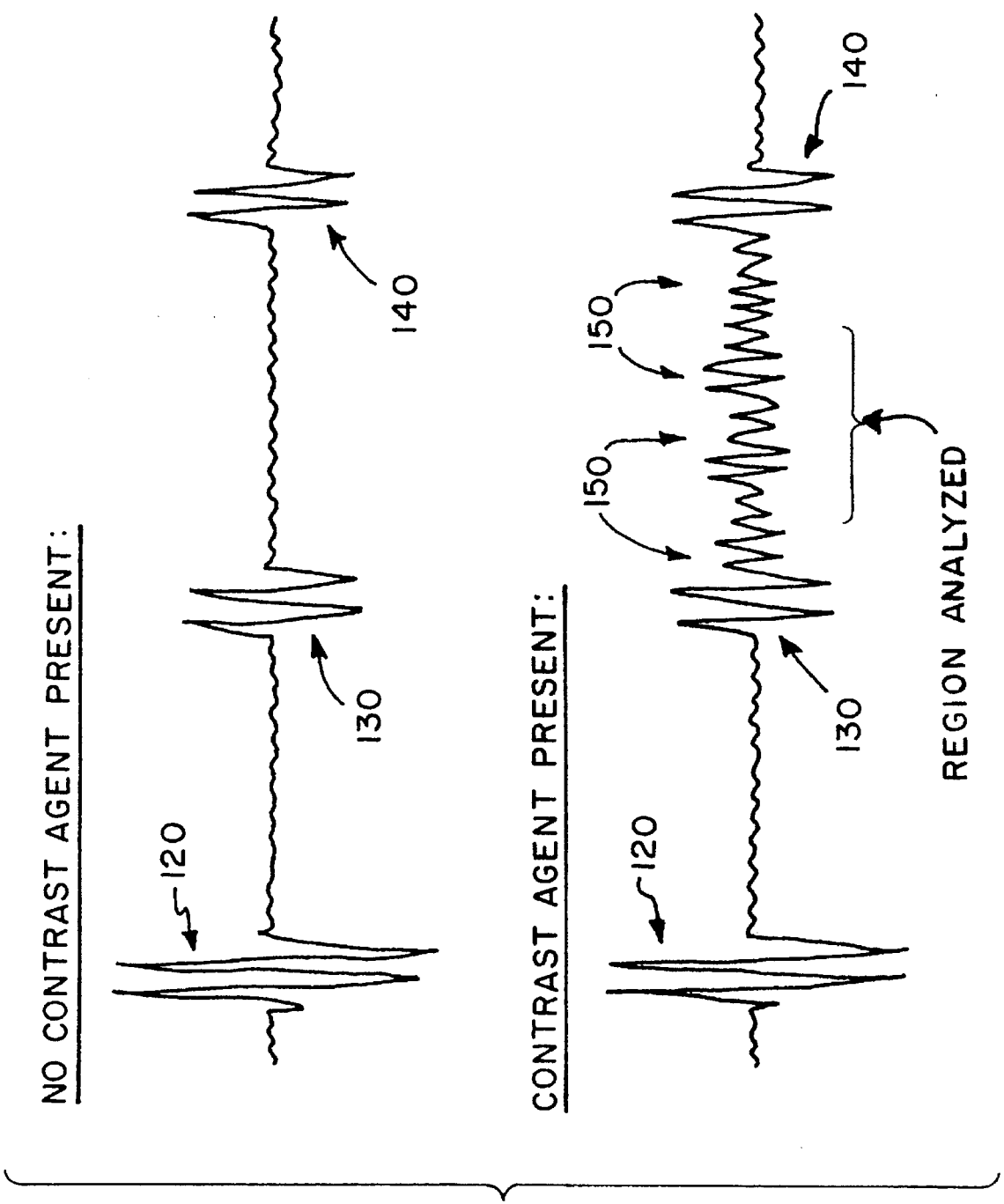
FIG. 5 is a pair of scan lines showing the region analyzed corresponding to the region of interest in the myocardium.

Referring to FIG. 5, only a portion of the RF sector scan lines is analyzed, corresponding to the region of interest in the myocardium. Peaks corresponding to the transducer burst 120, anterior wall echo 130, and the posterior wall echo 140 are present in both scans. However, only the scan in which the contrast agent is present indicates microsphere RF echos 150.

Figure 6:
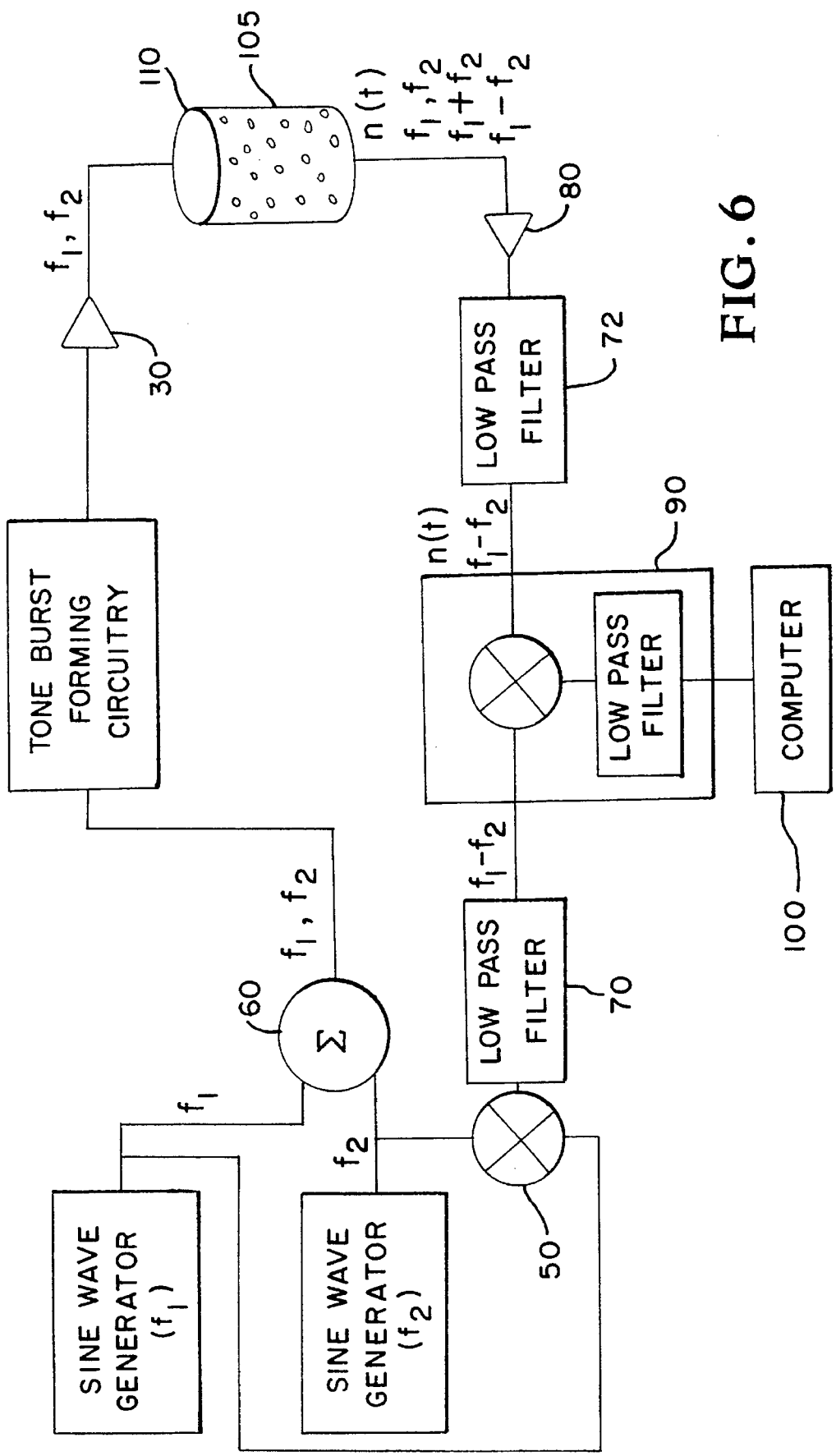
FIG. 6 is a block diagram of an embodiment of the present invention, including the summing circuit, with a generic interactive volume.

Referring to FIG. 6, since $f_1$ and $f_2$ are relatively close to each other, it is possible to use a single transducer 110. The intersection volume here is a cylinder 105 coaxially located beneath a single drive transducer. For this application it is possible to form an electrical drive signal by employing a summing circuit 60 to electrically add two electrical sine waves of different frequencies ($f_1$, $f_2$) together to form the electrical drive voltage.

Although the present invention has been illustrated with reference to human applications, it should be understood by those skilled in the art of ultrasonic imaging that the present invention could also be used in a variety of applications in which the ultrasonic detection of fluids is contemplated. For example, the present invention could be used in animals, plant systems and in a variety of industrial flow processes.

Many modifications, improvements and substitutions will be apparent to the skilled artisan in view of the foregoing description without departing from the spirit and scope of the present invention as described in the specification and defined in the following claims. Thus, it is to be understood that, within the scope of the appended claims, the invention may be practiced other than as specifically described hereinabove.

What is claimed is:

1. An apparatus for detecting the presence of ultrasonically relative microsphere contrast agents in a fluid, comprising:

means for directing ultrasonic energy into a region of the fluid at a first discrete frequency, the first frequency being approximately at a resonant frequency of the microspheres in the range of 1 MHz–30 MHz;

means for simultaneously directing ultrasonic energy into the region of fluid at a second discrete frequency that is also an approximate resonant frequency of the microspheres, wherein the microspheres in the fluid interact to emit sum and difference frequencies; and means for detecting the sum and difference frequencies.

2. The apparatus of claim 1 wherein the directing means for the ultrasonic energy at the first frequency is a transducer.

3. The apparatus of claim 2 wherein the directing means for the ultrasonic energy at the second frequency is a transducer.

4. The apparatus of claim 3 wherein the detecting means is a receive transducer.

5. An apparatus for measuring the presence of ultrasonically reflective microsphere contrast agents in a living body fluid, comprising:

means for injecting microbubble contrast agents into a living body;

means for directing ultrasonic energy into a region of the body fluid at a first discrete frequency, the first frequency being approximately at a resonant frequency of the microspheres in the range of 1 MHz–30 MHz;

means for simultaneously directing ultrasonic energy into the region of body fluid at a second discrete frequency that is also an approximate resonant frequency of the microspheres, wherein the microspheres interact to emit sum and difference frequencies; and means for detecting the sum and difference frequencies.

6. The apparatus of claim 5 wherein the directing means for the ultrasonic energy at the first frequency is a transducer.

7. The apparatus of claim 6 wherein the directing means for the ultrasonic energy at the second frequency is a transducer.

8. The apparatus of claim 7 wherein the detecting means is a receive transducer.

9. An method for detecting the presence of ultrasonically reflective microsphere contrast agents in a fluid, comprising:

directing ultrasonic energy into a region of the fluid at a first frequency, the first discrete frequency being approximately at a resonant frequency of the microspheres in the range of 1 MHz–30 MHz;

simultaneously directing ultrasonic energy in to the region of fluid at a second discrete frequency that is also an approximate resonant frequency of the microspheres, wherein the microspheres in the fluid interact to emit sum and difference frequencies; and detecting the sum and difference frequencies.

10. A method for detecting the presence of ultrasonically reflective microsphere contrast agents in a body fluid, comprising the steps of:

injecting microbubble contrast agents into a living body;

directing ultrasonic energy into a region of the body fluid at a first discrete frequency, the first frequency being approximately at a resonant frequency of the microspheres in the range of 1 MHz–30 MHz;

simultaneously directing ultrasonic energy into the body fluid region at a second discrete frequency that is also an approximate resonant frequency of the microspheres, such that the microspheres interact to emit sum and difference frequencies; and detecting the mixed frequencies generated by interaction of the resonant microspheres with ultrasonic energy at the first and second frequencies.

11. A method for detecting the presence of ultrasonically reflective microsphere contrast agents in a body fluid as in claim 10 wherein said means for injecting microbubble contrast agents further comprise a means for injecting albumin-coated microbubble contrast agents.

* * * * *